United States Patent [19]

Arai et al.

[11] Patent Number: 4,737,563

[45] Date of Patent: Apr. 12, 1988

[54] METHOD FOR THE PREPARATION OF AN ω,ω-DIHYDROORGANOPOLYSILOXANE

[75] Inventors: Masatoshi Arai; Shinichi Sato, both of Gunma, Japan

[73] Assignee: Shin-Etsu Chemical Co., Ltd., Tokyo, Japan

[21] Appl. No.: 944,751

[22] Filed: Dec. 22, 1986

[30] Foreign Application Priority Data

Dec. 27, 1985 [JP]  Japan ................................ 60-298135

[51] Int. Cl.$^4$ .............................................. C08G 77/02
[52] U.S. Cl. ...................................... 528/32; 525/478; 528/31; 528/34; 556/470
[58] Field of Search ....................... 525/478; 556/470; 528/32, 34, 31

[56] References Cited

U.S. PATENT DOCUMENTS 4,180,642  12/1979  Takago et al. ........................ 528/34

Primary Examiner—Melvyn I. Marquis
Attorney, Agent, or Firm—Jules E. Goldberg

[57] ABSTRACT

A novel method is proposed for the synthesis of an organopolysiloxane having two hydrogen atoms directly bonded to the same silicon atom at the molecular chain end. The method comprises mixing a dihydro isopropenyloxy silane with an organosilicon compound having at least one silanolic hydroxy group so that a condensation reaction takes place between the isopropenyloxy group of the former reactant and the silanol group of the latter reactant forming acetone as a by-product. The method is advantageous in respect of the absence of any acidic or basic by-product contained in the product as an impurity in the conventional methods.

3 Claims, 3 Drawing Sheets

METHOD FOR THE PREPARATION OF AN ω,ω-DIHYDROORGANOPOLYSILOXANE

BACKGROUND OF THE INVENTION

The present invention relates to a method for the preparation of an organopolysiloxane having two hydrogen atoms directly bonded to the same silicon atom at the molecular chain end, which is referred to as an ω,ω-dihydroorganopolysiloxane hereinbelow, or, more particularly, to a method for the preparation of an ω,ω-dihydroorganopolysiloxane free from the problem in the prior art method due to the acidic or basic by-product produced by the reaction.

As is well known in the art of silicones, ω,ω-dihydroorganopolysiloxanes are reactive and useful as an intermediate for the synthesis of various kinds of organosilicon compounds and as an ingredient in organopolysiloxane compositions, e.g. cellular foamed bodies of organopolysiloxane compositions, curable by the irradiation with actinic rays, e.g. ultraviolet light, or by the mechanism of so-called hydrosilation which is a reaction between silicon-bonded hydrogen atoms and aliphatic unsaturation in the other constituent in the composition.

Such an ω,ω-dihydroorganopolysiloxane is synthetically prepared in the prior art by the method disclosed, for example, in Japanese Patent Publication No. 45-9474, according to which a dihydro monohalogeno silane of the general formula $RSiH_2X$, where R is a monovalent hydrocarbon group and X is a halogen atom, acyloxy group or amino group, is mixed with an organo-silicon compound having a silanolic hydroxy group such as an α,ω-dihydroxy diorganopolysiloxane of the general formula $HO-(-SiR_2-O-)_n-H$, in which R has the same meaning as defined above and n is a positive integer, so that a condensation reaction takes place between these two reactants to form a linkage of $RH_2Si-O-SiR_2-$ at each of the molecular chain ends with formation of HX, such as a hydrogen halide, carboxylic acid and amine, as the by-product.

The above mentioned conventional method for the preparation of an ω,ω-dihydroorganopolysiloxane is sometimes disadvantageous because the by-product HX can be removed completely from the product only by a very troublesome and time-consuming purification process while even a trace amount of such an acidic or basic impurity is very detrimental in certain applications of the ω,ω-dihydroorganopolysiloxane.

SUMMARY OF THE INVENTION

Accordingly, the present invention has an object to provide a novel and improved method for the preparation of an ω,ω-dihydroorganopolysiloxane free from the above mentioned problems in the prior art method due to the acidic or basic by-product formed in the synthetic reaction.

Thus, the method for the preparation of an ω,ω-dihydroorganopolysiloxane provided by the present invention comprises mixing a dihydro isopropenyloxy silane compound represented by the general formula $$RH_2Si(-O-CCH_3=CH_2), \quad (I)$$

in which R is a substituted or unsubstituted monovalent hydrocarbon group, with an organosilicon compound having at least one silanolic hydroxy group bonded to a silicon atom.

The reaction proceeds between the isopropenyloxy group in the silane compound of the formula (I) and the silanolic hydroxy group in the silanol-containing organosilicon compound to form a siloxane linkage producing acetone as a by-product. The reaction proceeds so easily even at room temperature or even below so that the reaction mixture is not necessarily heated.

DETAILED DESCRIPTION OF THE PREFERRED EMBODIMENTS

Figure 1:
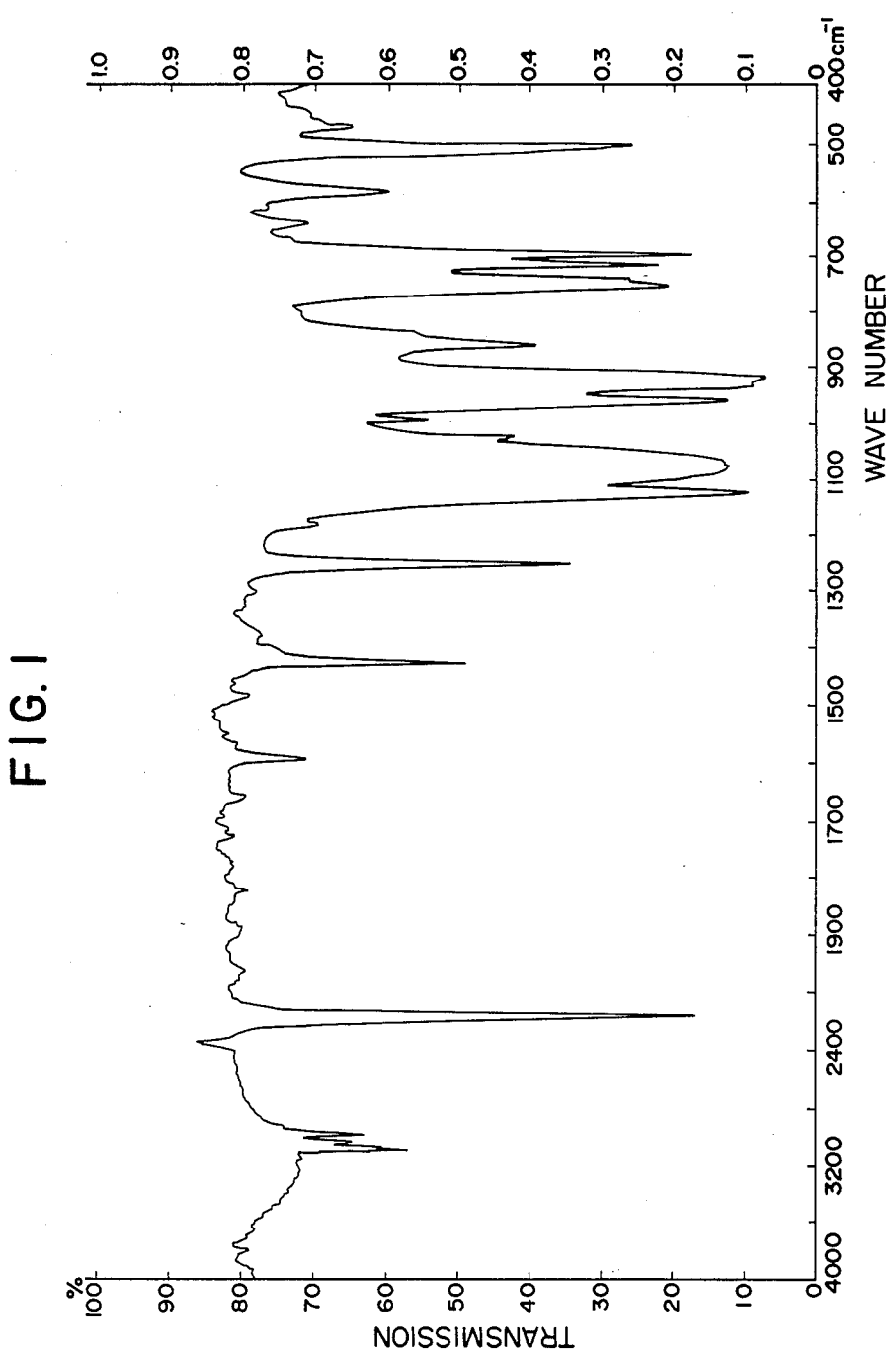
FIGS. 1, 2 and 3 are each an infrared absorption spectrum of the product obtained in Examples 1, 2 or 3, respectively.

As is understood from the above given summary of the invention, the inventive method characteristically utilizes the condensation reaction of a dihydro isopropenyloxy silane of the general formula (I) and a silanol-containing organosilicon compound. The condensation reaction proceeds between the isopropenyloxy groups in the former reactant and the silanolic hydroxy groups in the latter reactant to form a siloxane linkage with acetone as the only condensation product according to the reaction equation $$RH_2Si-O-CCH_3=CH_2 + HO-Si \longrightarrow RH_2Si-O-Si-+CH_3-CO-CH_3$$

so that an organopolysiloxane compound having two hydrogen atoms directly bonded to one of the terminal silicon atoms is obtained.

The symbol R in the general formula (I) representing the first reactant denotes a substituted or unsubstituted monovalent hydrocarbon group exemplified by alkyl groups, e.g. methyl, ethyl, propyl and butyl groups, cycloalkyl groups, e.g. cyclohexyl and cyclopentyl groups, alkenyl groups, e.g. vinyl and allyl groups, aryl groups, e.g. phenyl, tolyl, xylyl and naphthyl groups and aralkyl groups e.g. benzyl and phenanthryl groups, as well as substituted monovalent hydrocarbon groups obtained by replacing a part or all of the hydrogen atoms in the above named hydrocarbon groups with substituent atoms and/or groups such as halogen atoms, cyano groups and the like exemplified by chloromethyl, trichloropropyl and trifluoropropyl groups. Particular examples of the dihydro isopropenyloxy silane compound include methyl isopropenyloxy silane, ethyl isopropenyloxy silane, phenyl isopropenyloxy silane, 3,3,3-trifluoropropyl isopropenyloxy silane, 2-cyanoethyl isopropenyloxy silane and the like.

The second reactant brought into reaction with the above described dihydro isopropenyloxy silane compound is an organosilicon compound having a silanolic hydroxy group. The compound may be either an organosilane compound or an organopolysiloxane compound without particularly influencing the reaction with the first reactant. The organic groups bonded to the silicon atom or atoms in the organosilicon compound may be selected from the same class of the groups given above as the examples of the monovalent hydrocarbon group denoted by R in the general formula (I). When the organosilicon compound is an organopolysiloxane compound, the degree of polymerization thereof is not particularly limitative but should preferably not exceed 1000 in view of the reactivity with the first reactant.

Several of the particular examples of the silanol-containing organosilicon compound include organosilane compounds such as trimethyl silanol, vinyl dimethyl silanol, triphenyl silanol, diphenyl silane diol and the like and organopolysiloxane compounds such as those expressed by the following formulas, in which the symbols Me, Et, Pr, Vi and Ph denote methyl, ethyl, propyl, vinyl and phenyl groups, respectively, and the subscript n is a positive integer of 2 to 1000: HO—(—SiMe$_2$—O—)$_n$—H; HO—[—SiMe(CH$_2$CH$_2$CF$_3$)—O—]$_n$—H; HO—(—SiPh$_2$—O—)$_n$—H; HO—(—SiMePh—O—)$_n$—H; HO—(—SiEt$_2$—O—)$_n$—H; HO—(—SiPr$_2$—O—)$_n$—H; and HO—(—SiMeVi—O—)$_n$—H. Silanol-containing organopolysiloxanes having a similar to but somewhat more complicated molecular structure than the above given ones can be prepared by the cohydrolysis of two kinds or more of chlorine-containing silanes including triorganochlorosilanes, diorganodichlorosilanes, monoorganotrichlorosilanes and silicon tetrachloride and can be used as the second reactant in the inventive method.

In performing the reaction of the above described two reactants according to the inventive method, the reactants may be dissolved, according to need, in an organic solvent such as toluene, xylene, hexane and the like to form a reaction mixture. Since the reaction proceeds between an isopropenyloxy group and a silanolic hydroxy group, the mixing ratio of the first reactant to the second reactant should preferably be equimolar or nearly equimolar relative to the molar ratio of the isopropenyloxy groups in the first reactant to the silanol groups in the second reactant. The reaction can proceed at a temperature in the range from 0° to 50° C. or, in most cases, from 0° to 20° C. to give the desired product in a yield of 98% or higher based on the theoretical value.

After completion of the reaction, the reaction product should be purified according to need in order to isolate the ω,ω-dihydroorganopolysiloxane in a purified form as desired. Since the condensation product contained in the reaction mixture as a by-product is acetone, mere distillation of the mixture under a pressure of 50 mmHg or below is sufficient to completely remove the acetone.

The thus obtained ω,ω-dihydroorganopolysiloxane is industrially useful in many applications. For example, the hydrosilation reaction of the compound with allyl acrylate gives an organopolysiloxane having two 3-acryloxypropyl groups at one molecular chain end which can be an ingredient in a resin composition readily curable by the irradiation with ultraviolet light or electron beams. When the ω,ω-dihydroorganopolysiloxane is reacted by the hydrosilation reaction with a functional organic compound having a vinyl or allyl group, the resultant organopolysiloxane may have two functional groups at each of the molecular chain ends. Needless to say, the ω,ω-dihydroorganopolysiloxane as such is useful as a component of a room temperature-curable organopolysiloxane composition or a component of a silicone foamed body.

In the following, the method of the present invention is described in more detail by way of examples with a preceding description of the preparation of an isopropenyloxy silane compound.

Preparation of methyl isopropenyloxy silane

Into a four-necked flask of 1 liter capacity equipped with a stirrer, reflux condenser and thermometer were introduced 800 g of methyl bis(isopropenyloxy)silane, 0.5 g of iron (III) chloride and 0.5 g of N,O-bis(trimethylsilyl)acetamide and the mixture was heated for 8 hours at 120° C. under reflux. After completion of the reaction, the reaction mixture was distilled under normal pressure to give 196.5 g of a fraction boiling at 60° C. This product could be identified to be the desired methyl isopropenyloxy silane from the results of the gas chromatographic-mass spectrometric analysis to give a principal peak at a mass number of 102 as well as the NMR analysis, infrared absorption spectrophotometric (IR) analysis and elementary analysis to give the results as shown below. The yield was 38.0% of the theoretical value.

NMR analysis: δ 0.11 (t, Si—CH$_3$, 3H); δ 1.57 (s, C—CH$_3$, 3H); δ 3.91 (s, C=CH$_2$, 2H); δ 4.57 (q, Si—H, 2H).

IR analysis: 2160 cm$^{-1}$ (Si—H); 1650 cm$^{-1}$ (C=C).

Elementary analysis:

|  | C, % | H, % | Si, % |
| --- | --- | --- | --- |
| Calculated as C$_4$H$_{10}$OSi | 47.00 | 9.86 | 27.47 |
| Found | 46.9 | 9.6 | 27.7 |

EXAMPLE 1

Into a three-necked flask of 50 ml capacity equipped with a reflux condenser, thermometer and dropping funnel were introduced 5.4 g of diphenyl silane diol and 10.0 g of toluene and then 5.1 g of the methyl isopropenyloxy silane obtained in the above described preparation were added dropwise into the reaction mixture in the flask under agitation using an electromagnetic stirrer over a period of 10 minutes. Temperature of the reaction mixture was increased from 20° C. at the start to 25° C. at the end of the dropwise addition of the silane compound.

After completion of the dropwise addition of the methyl isopropenyloxy silane, agitation of the reaction mixture was continued for 4 hours to complete the reaction without particularly controlling the temperature and then the reaction mixture was distilled under a reduced pressure of 4 mmHg to give 5.6 g of a fraction boiling at 123° to 125° C. under a pressure of 4 mmHg and having a refractive index of 1.512 at 20° C. This product could be identified to be 1,5-dimethyl-3,3-diphenyl trisiloxane from the results of the gas chromatographic-mass spectrometric (GC-MS) analysis, NMR analysis, infrared absorption spectrophotometric (IR) analysis and elementary analysis shown below. The yield was 74% of the theoretical value.

GC-MS analysis: principal peak at mass number 304.

NMR analysis: δ 0.41 (t, Si—CH$_3$, 6H); δ 4.84 (q, Si—H, 4H); δ 7.40 (m, arom, 10H).

IR analysis: See FIG. 1. 2150 cm$^{-1}$ (Si—H); 1590 cm$^{-1}$ (arom); 1070 cm$^{-1}$ (Si—O—Si).

Elementary analysis:

|  | C, % | H, % | Si, % |
| --- | --- | --- | --- |
| Calculated as C$_{14}$H$_{20}$O$_2$Si$_3$ | 55.2 | 6.6 | 27.7 |
| Found | 55.3 | 6.4 | 27.9 |

EXAMPLE 2

Into a three-necked flask of 50 ml capacity equipped with a reflux condenser, thermometer and dropping funnel were introduced 5.8 g of 1,1,3,3-tetraisopropyl disiloxane-1,3-diol and 10.0 g of toluene and then 5.1 g of the methyl isopropenyloxy silane obtained in the above described preparation were added dropwise into the reaction mixture in the flask under agitation using an electromagnetic stirrer over a period of 10 minutes. Temperature of the reaction mixture was increased from 23° C. at the start to 45° C. at the end of the dropwise addition of the silane compound.

After completion of the dropwise addition of the methyl isopropenyloxy silane, agitation of the reaction mixture was continued for 2 hours to complete the reaction without particularly controlling the temperature and then the reaction mixture was distilled under a reduced pressure of 4 mmHg to give 6.2 g of a fraction boiling at 102° to 105° C. under a pressure of 4 mmHg and having a refractive index of 1.431 at 20° C. This product could be identified to be 1,7-dimethyl-3,3,5,5-tetraisopropyl tetrasiloxane from the results of the gas chromatographic-mass spectrometric (GC-MS) analysis, NMR analysis, analysis by infrared absorption sspectrophotometry (IR) and elementary analysis shown below. The yield was 67% of the theoretical value.

Figure 2:
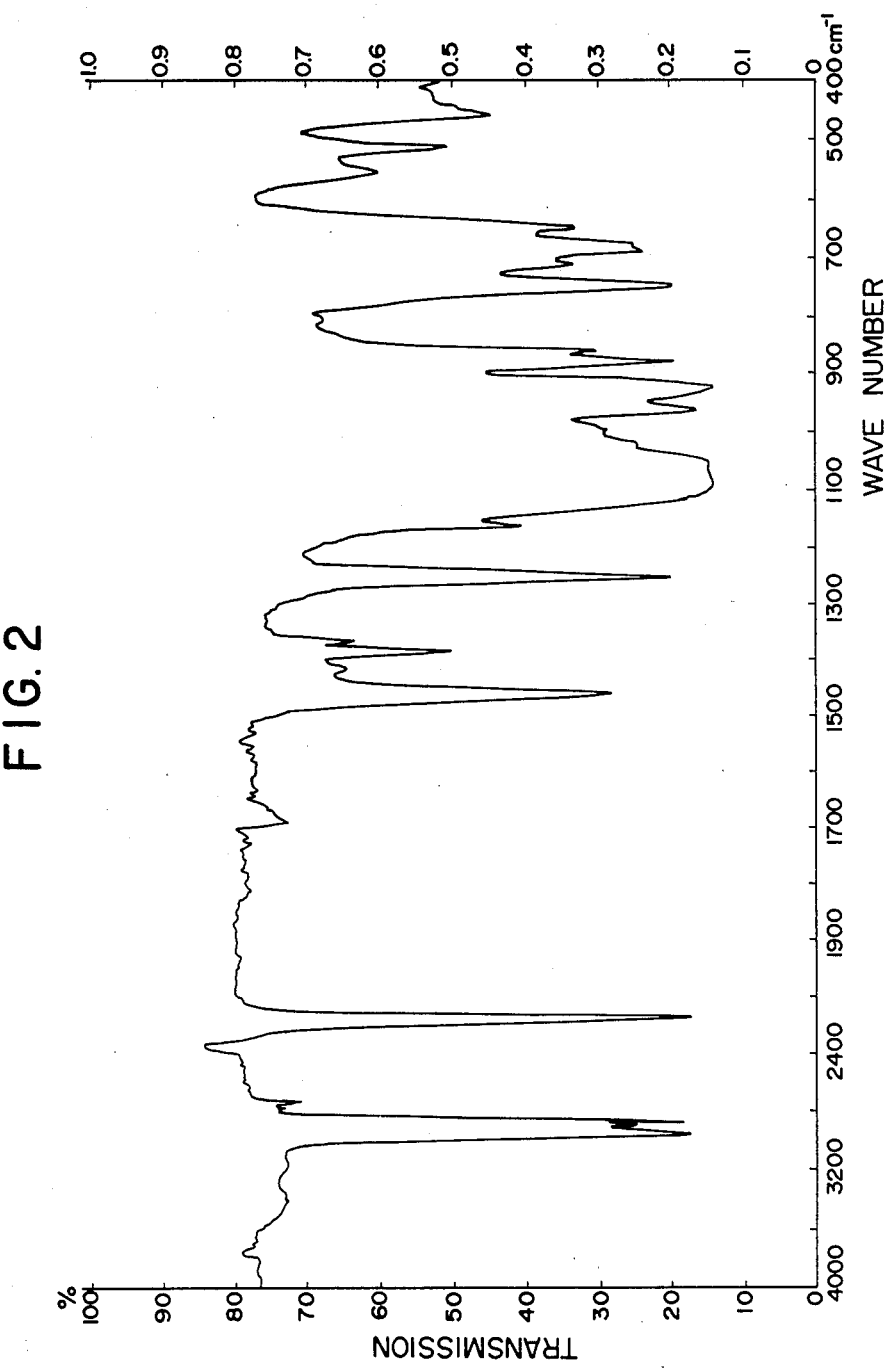

GC-MS analysis: principal peak at mass number 366.
NMR analysis: $\delta$ 0.37 (t, Si—CH$_3$, 6H); $\delta$ 1.03 (s, C—CH$_3$, 24H); $\delta$ 4.71 (q, Si—H, 4H).
IR analysis: See FIG. 2. 2150 cm$^{-1}$ (Si—H); 1590 cm$^{-1}$ (arom); 1070 cm$^{-1}$ (Si—O—Si).
Elementary analysis:

|  | C, % | H, % | Si, % |
|---|---|---|---|
| Calculated as C$_{14}$H$_{38}$O$_3$Si$_4$ | 45.8 | 10.4 | 30.6 |
| Found | 45.7 | 10.1 | 30.8 |

EXAMPLE 3

Into a four-necked flask of 500 ml capacity equipped with a reflux condenser, thermometer and dropping funnel were introduced 300 g of an $\alpha,\omega$-dihydroxy dimethylpolysiloxane having a viscosity of 700 centistokes at 20° C. and containing 0.01 mole of silanolic hydroxy groups per 100 g and then 3.1 g of the methyl isopropenyloxy silane obtained in the above described preparation were added dropwise into the reaction mixture in the flask under agitation using an electromagnetic stirrer over a period of 10 minutes. Temperature of the reaction mixture was increased from 23° C. at the start to 45° C. at the end of the dropwise addition of the silane compound. Agitation of the reaction mixture was further continued for additional two hours to complete the reaction. The gas chromatographic analysis of the reaction mixture after completion of the reaction in the above described manner indicated substantial absence of the starting methyl isopropenyloxy silane.

Figure 3:
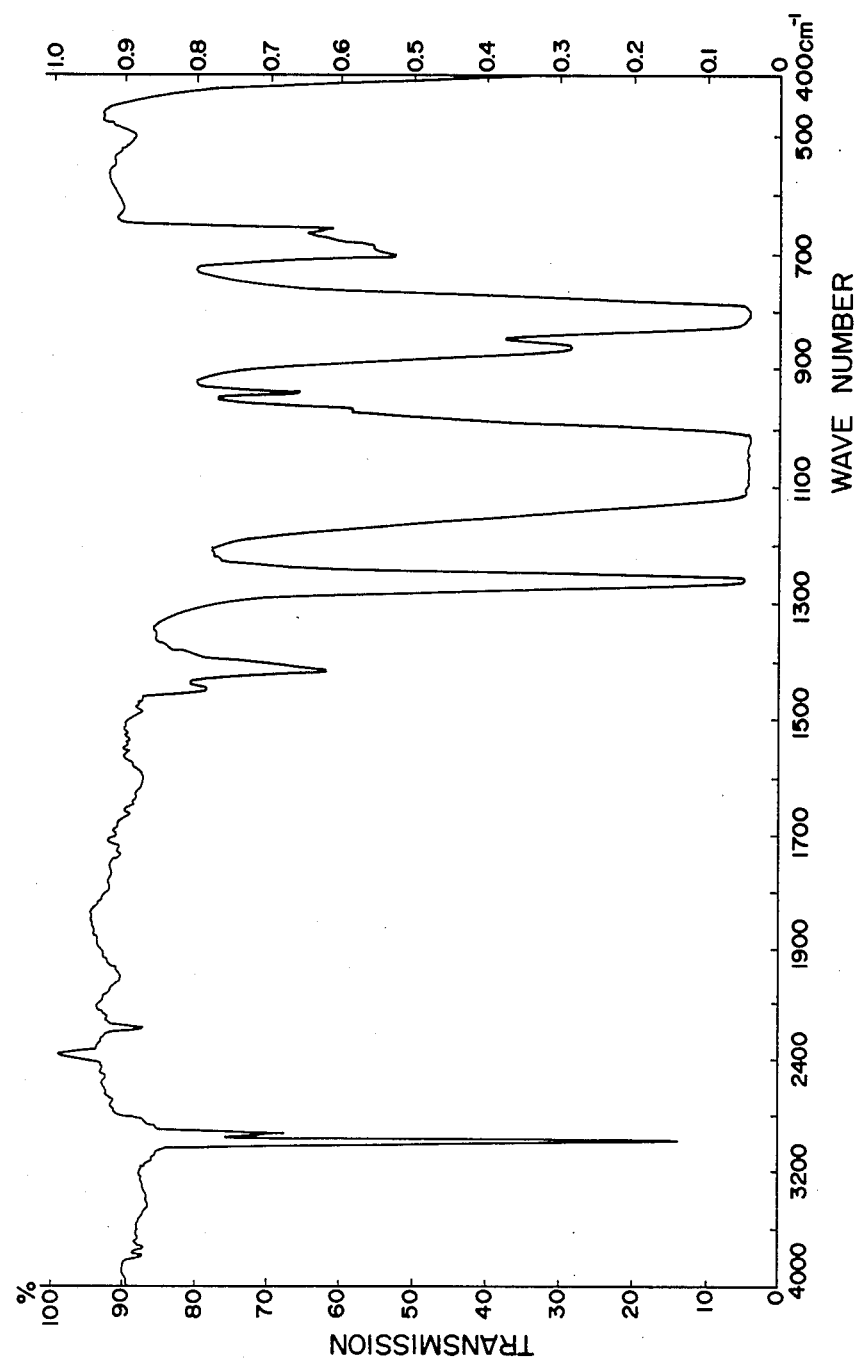

The thus obtained reaction product after stripping of acetone by distillation gave an infrared absorption spectrum shown in FIG. 3 having an absorption band at a wave number of 2150 cm$^{-1}$ assignable to Si—H and could be concluded to be an $\alpha,\alpha,\omega,\omega$-tetrahydro dimethylpolysiloxane having an average degree of polymerization of about 200 to 300.

What is claimed is:

1. A method for the preparation of an $\omega,\omega$-dihydroorganopolysiloxane which comprises mixing a dihydro isopropenyloxy silane compound represented by the general formula

RH$_2$Si(—O—CCH$_3$=CH$_2$), in which R is a substituted or unsubstituted monovalent hydrocarbon group, with an organosilicon compound having at least one silanolic hydroxy group bonded to a silicon atom.

2. The method as claimed in claim 1 wherein the dihydro isopropenyloxy silane is mixed with the organosilicon compound having at least one silanolic hydroxy group bonded to a silicon atom in such a ratio that the amount of the hydroxy groups in the organosilicon compound is substantially equimolar to the isopropenyloxy groups in the dihydro isopropenyloxy silane compound.

3. The method as claimed in claim 1 wherein the group denoted by R is selected from the class consisting of alkyl groups, cycloalkyl groups, alkenyl groups, aryl groups and aralkyl groups.

* * * * *